United States Patent
Okubo et al.

(10) Patent No.: US 6,948,356 B2
(45) Date of Patent: Sep. 27, 2005

(54) VISCOELASTICITY MEASURING INSTRUMENT

(75) Inventors: Nobuaki Okubo, Chiba (JP); Jun Nagasawa, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/913,110

(22) Filed: Aug. 6, 2004

(65) Prior Publication Data

US 2005/0126267 A1 Jun. 16, 2005

(30) Foreign Application Priority Data

Aug. 11, 2003 (JP) .................................. 2003-207074
Aug. 3, 2004 (JP) .................................. 2004-226411

(51) Int. Cl.[7] .............................................. G01N 11/00
(52) U.S. Cl. ................................................... 73/54.43
(58) Field of Search ........................... 73/54.02, 54.41, 73/54.43

(56) References Cited

U.S. PATENT DOCUMENTS

| | | | | | |
|---|---|---|---|---|---|
| 3,514,427 | A | * | 5/1970 | Owens | 524/524 |
| 3,901,074 | A | * | 8/1975 | Douglas | 73/657 |
| 3,903,734 | A | * | 9/1975 | Douglas | 73/579 |
| 4,418,573 | A | * | 12/1983 | Madigosky et al. | 73/574 |
| 6,484,567 | B1 | * | 11/2002 | Hajduk et al. | 73/54.37 |
| 6,609,428 | B2 | * | 8/2003 | Hull | 73/789 |
| 6,644,101 | B2 | * | 11/2003 | Hajduk et al. | 73/54.37 |
| 6,655,194 | B2 | * | 12/2003 | Hajduk et al. | 73/54.37 |
| 6,668,622 | B2 | * | 12/2003 | Hajduk et al. | 73/54.37 |
| 6,681,618 | B2 | * | 1/2004 | Hajduk et al. | 73/54.37 |
| 6,829,951 | B2 | * | 12/2004 | Putman et al. | 73/862.321 |
| 6,845,671 | B2 | * | 1/2005 | Hull | 73/574 |

FOREIGN PATENT DOCUMENTS

| | | | | | |
|---|---|---|---|---|---|
| JP | | 04160249 | A | * 6/1992 | F16F/15/02 |

OTHER PUBLICATIONS

Micro Materials "The Nano Test" (web document), pp. 1–16.*

Lakes et al. "Extreme damping in composite materials with negative-stiffness inclusions" Nature, vol. 410, pp. 565–567, Mar. 29, 2001.*

Ziokowski et al. "The influence of the transmission function of the impedance head on the measurement of the complex elastic modulus of a viscoelastic beam by the driving point impedance method," Journal of Sound and Vibration, Abstract, Jan. 22, 1982.*

* cited by examiner

*Primary Examiner*—Hezron Williams
*Assistant Examiner*—John Fitzgerald
(74) *Attorney, Agent, or Firm*—Adams & Wilks

(57) ABSTRACT

A viscoelasticity measuring instrument for measuring a viscoelasticity of a sample has a temperature detection control unit for obtaining, prior to a practical measurement operation, a measurement executable temperature range for the sample by an experimental temperature control operation and application of AC power. A main measurement control unit carries out a viscoelasticity measurement operation within the temperature range obtained by the temperature detection control unit.

16 Claims, 7 Drawing Sheets

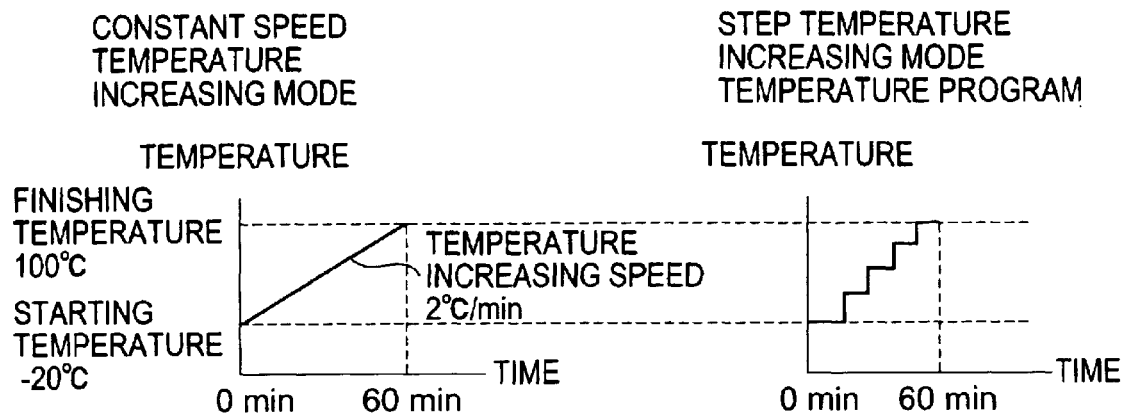

VISCOELASTICITY MEASURING INSTRUMENT

BACKGROUND OF THE INVENTION

1. Field of the Invention

The present invention relates to a viscoelasticity measuring instrument adapted to apply AC stress or strain to a sample, detect the strain or stress occurring in the sample during this time and measure the viscoelasticity of the sample on the basis of the correlation between the stress and strain.

2. Background Information

A conventional instrument (disclosed in, for example, JP-A-11-218483) is known which is adapted to apply AC stress or strain to a sample, detect the strain or stress occurring in the sample during this time and measure a complex elastic modulus of the sample on the basis of the correlation between the stress and strain.

This related art instrument is provided with a structure for displaying an error mark of "non-measurement-executable" when the strain occurring in a sample is too small or too large to normally calculate a viscoelasticity of the sample, and immediately finishing the measurement operation, or a structure for continuing the measurement operation ignoring the error mark of "non-measurement-executable".

In general, a sample to be measured becomes softer when the temperature thereof becomes higher. Especially, in the case of a resin sample, phenomena, such as glass transition and melting, occur, i.e., the resin is softened at a high temperature. Conversely, in the case of a thermosetting resin, the resin gels and is soft at a low temperature, and becomes hard at a high temperature in some cases due to a hardening reaction. In order to measure the viscoelasticity of an unknown sample, a temperature range in which the hardness of the sample can be measured cannot be determined unless the measuring of the sample is practically done.

Therefore, in a related art instrument, the measurement of an unknown sample is conducted at a temperature in an experimentally estimated range. When the error mark of "non-measurement-executable" is displayed during the measurement, a method of trial and error in which an operator puts detection and measurement operations into practice repeatedly while changing the range of temperature little by little was carried out.

As a result, in order to measure an unknown sample, it is necessary that measurement operations be conducted many times by way of trial until a temperature range in which the measurement of the sample can be conducted, so that much labor and much time were taken.

In the case of the structure in which measurement keeps being conducted with an error mark displayed ignored, wasteful measurement is necessarily carried out in repetition, so that a measuring efficiency is low.

An object of the present invention is to solve these inconveniences, i.e., to reduce the measuring labor and finding out a measurement executable temperature at a high speed and with a high accuracy.

SUMMARY OF THE INVENTION

To solve these problems, the viscoelasticity measuring instrument according to the present invention has a function of conducting, prior to the practical measurement of a sample, a detection measurement for finding out a temperature range, in which the measurement of the sample can be conducted, by an experimental sample temperature control operation and the application of AC power to the sample, and conducting a practical measurement operation at a temperature in the temperature range obtained by the detection measurement.

The viscoelasticity measuring instrument according to the present invention has a heating furnace provided around a sample and adapted to heat the sample, a temperature program function generator adapted to generate a temperature program function in accordance with a set temperature program comprised of a temperature function with respect to a temperature range and a time period, a heating furnace control unit connected to the temperature program function generator and adapted to control the temperature in the heating furnace on the basis of the temperature program function outputted from the temperature program function generator, means for applying stress to the sample, and an AC power program function generator adapted to generate a sine wave signal as an AC power program function in accordance with a set AC power program containing of a frequency and a frequency mode. An AC power control unit is connected to the AC power program function generator and is adapted to output a sine wave stress signal on the basis of the AC power program function outputted form the AC power program function generator and to control the stress application means so that the sine wave stress is outputted to the stress application means. A displacement detector is adapted to detect as a sine wave strain signal the displacement of the sample occurring due to the application of sine wave stress from the stress application means thereto. A viscoelastic modulus calculator is adapted to calculate a complex elastic modulus of the sample on the basis of the correlation between a sine wave stress signal outputted from the AC power control unit and a sine wave strain signal outputted from the displacement detector and output it as a viscoelastic modulus signal to output an error mark of "non-measurement-executable" when the complex elastic modulus exceeds a preset upper limit reference level or falls below a preset lower limit reference level. A measurement executable temperature detection measurement control unit is adapted to set prior to a practical measurement operation a predetermined temperature program in the temperature program function generator, and a predetermined AC power in the AC power program function generator, operate the temperature program function generator and AC power program function generator and monitor an output from the viscoelastic modulus calculator, and keep conducting the measurement operation while the error mark of "non-measurement-executable" is displayed and output an actual temperature as an upper limit temperature or a lower limit temperature at which the elastic modulus of the sample can be measured when the error mark of "non-measurement-executable" ceases to be displayed. A main measurement control unit is adapted to conduct a practical measurement operation by rewriting the temperature range in the temperature program set by the measurement executable temperature detection measurement control unit to a measurement executable temperature range based on the measurement executable upper limit temperature or lower limit temperature outputted from the measurement executable temperature detection measurement control unit, resetting the temperature program to a desired temperature program and AC power program, outputting the programs to the temperature program function generator and AC power program function generator, and monitoring an output from the viscoelastic modulus calculator.

BRIEF DESCRIPTION OF THE DRAWINGS

FIG. 2 is a drawing showing an example of a temperature program;

FIG. 3 is a drawing showing constituent elements of an AC power program;

DETAILED DESCRIPTION OF THE PREFERRED EMBODIMENTS

Embodiments of the present invention will now be described with reference to the drawings.

Figure 1:
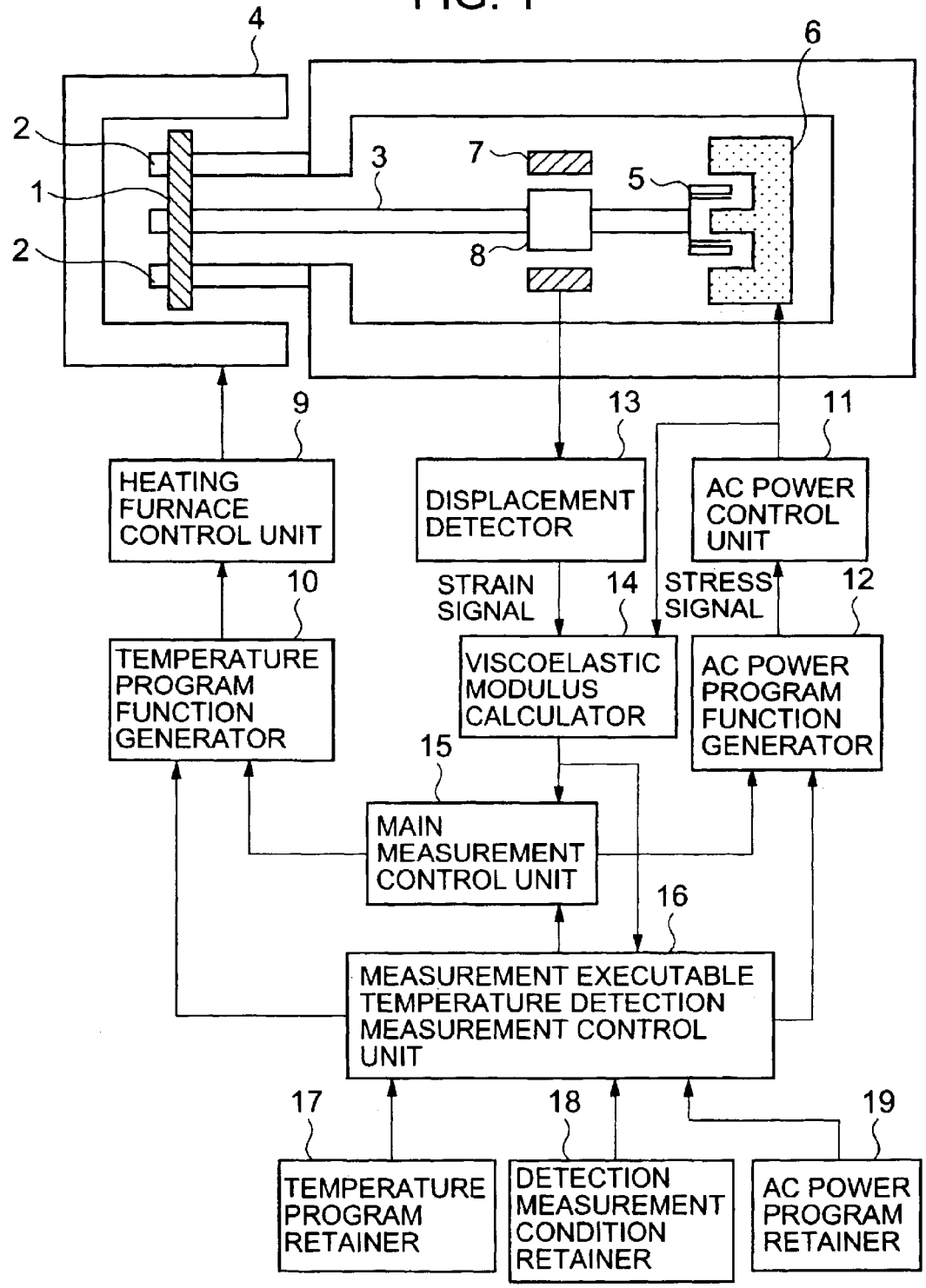
FIG. 1 is a schematic sectional view of a viscoelasticity measuring instrument showing an embodiment of the present invention.

Referring to FIG. 1, a reference numeral 1 denotes a sample, both end portions of which are held by chucks 2. A probe 3 is held elastically in a casing, and fixed at one end portion thereof to a central portion of the sample 1, a coil 5 being fixed to the other end portion of the probe 3. The coil 5 and a magnet 6 disposed so as to surround the coil 5 constitute an AC power generator. The probe 3 is mounted firmly at an intermediate portion thereof with a core 8, and the relative displacement of the probe 3 is detected between the core 8 and a differential transformer 7 disposed so as to surround the core 8.

Various kinds of modes of displacement, such as bending, tension, compression, shearing and torsion of the sample 1 can be taken depending upon the shape of the chucks 2.

A temperature program function generator 10 is adapted to output a temperature program signal in accordance with a set temperature program. A heating furnace control unit 9, as a first control unit, is adapted to control a heating furnace 4, as heating means, on the basis of an output from the temperature program function generator 10.

An AC power program function generator 12 is adapted to output a frequency signal in accordance with a set AC power program. An AC power control unit 11, as a second control unit, is adapted to control the AC power generator, which is made of the coil 5 and magnet 6, on the basis of an output from the AC power program function generator 12.

A displacement detector 13 is adapted to output the displacement occurring between the core 8 and differential transformer 7 as a strain signal.

A viscoelastic modulus calculator 14 is adapted to receive the strain signal from the displacement detector 13 and a stress signal from the AC power control unit 11, calculate a complex elastic modulus on the basis of the correlation between the strain and stress, and output the resultant complex elastic modulus. When the elastic modulus cannot be calculated correctly for the reason that the strain signal is too large or too small, an error mark of "non-measurement-executable" is outputted.

A measurement control unit 15, as a fourth control unit, is adapted to carry out the heating of the sample 1 and the application of AC power thereto by controlling the temperature program function generator 10 and AC power program function generator 12, conduct the measurement of the sample, and record an output from the viscoelastic modulus calculator 14 as measurement data.

A temperature program retainer 17 is adapted to retain the temperature program. The temperature program includes temperature increasing and cooling rates and measuring temperature ranges, which can be selected by an operator. The methods of temperature increasing and cooling the temperature program include a method of an equal speed mode and a method of a step mode. The examples of the equal speed mode and step mode are shown in FIG. 2. Although a temperature program of an equal speed mode will be described in this embodiment, even a temperature program of a step mode can also be carried out practically in the same manner. It is also possible to form differently the temperature program mode for the detection measurement and that for the main measurement. In the measurement executable temperature detection operation, the temperature program is set so that the temperature program is started at a temperature estimated to be at a non-measurement executable level due to a too high hardness of the sample. In order to subject a sample becoming soft at a high temperature to a temperature increasing measurement, a starting temperature is set lower, and, in order to subject a sample becoming soft at a low temperature to a cooling measurement operation, a starting temperature is set higher.

A detection measurement condition retainer 18 is adapted to retain the measurement condition for detection measurement. When the detection measurement operation is conducted in an equal speed mode just as in this embodiment, the detection measurement temperature increasing speed is maintained. The detection measurement condition is selectable by an operator. In order to conduct the detection of a measurement executable temperature accurately irrespective of the length of the required time, the detection temperature increasing speed is set low. In order to conduct the detection of a measurement executable temperature in a short period of time irrespective of the level of accuracy, the detection temperature increasing speed is set high.

An AC power program retainer 19 is adapted to retain the AC power program applied to the sample 1 during the measurement thereof. As shown in FIG. 3, the AC power program includes a frequency list having a plurality of frequencies, and frequency modes for selecting the method (applying sine waves continuously or applying one synthetic wave) of applying a plurality of frequencies to the sample, and these are selectable by the operator.

A measurement executable temperature detection measurement control unit 16, as a third control unit, is adapted to control a detection measurement operation for finding out a minimum temperature at which the measurement of the elastic module can be conducted.

The detection measurement operation is conducted by using the detection measurement temperature program and detection measurement AC power program.

The detection measurement temperature program has the same temperature range as the temperature program used in the main measurement operation, and the detection temperature increasing speed set in the detection measurement condition retainer 18.

Figure 4:
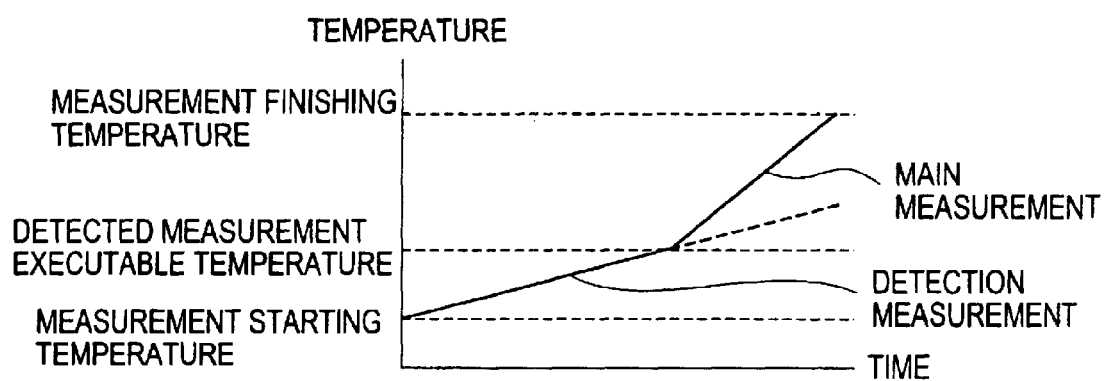
FIG. 4 shows an example 1 of a temperature control operation in the detection measurement and main measurement operations.
Figure 5:
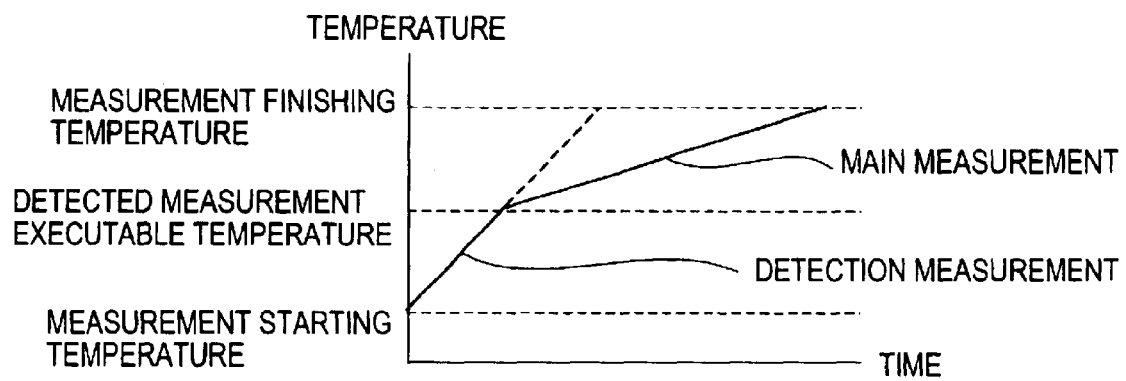
FIG. 5 shows an example 2 of a temperature control operation in the detection measurement and main measurement operations.
Figure 6:
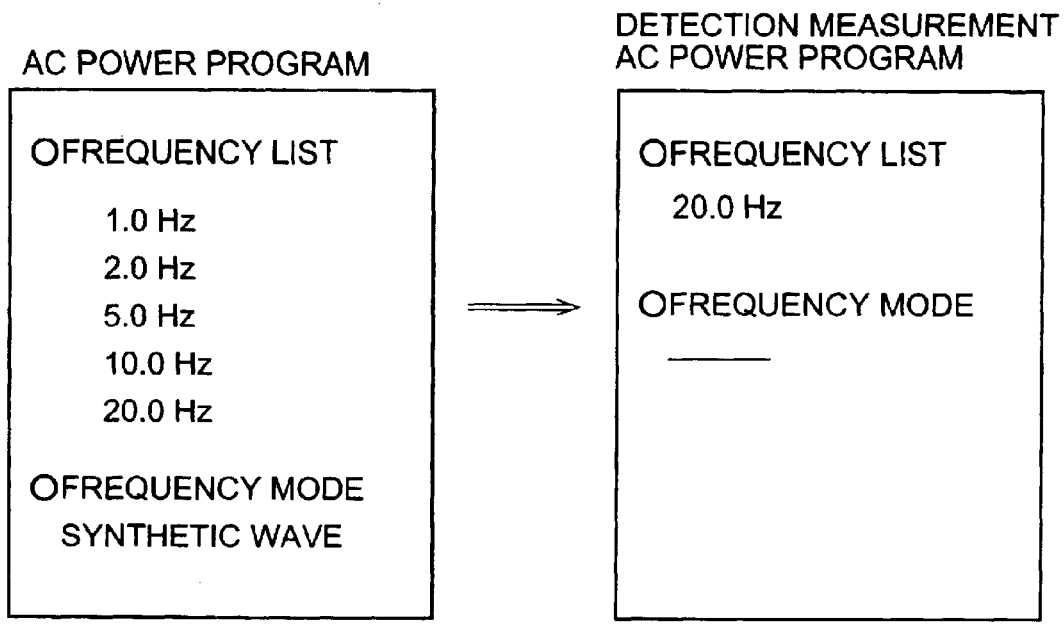
FIG. 6 is a drawing showing the relation between the AC power program and detection measurement AC power program.

FIGS. 4 and 5 show examples of temperature control operations in the detection measurement and main measurement of a sample. FIG. 4 shows an example in which the detection accuracy is increased by setting the detection temperature increasing speed lower than that for the main measurement operation. FIG. 5 shows an example in which the detection measurement is conducted in a short period of time by setting the detection temperature increasing speed higher than that for the main measurement operation.

Figure 7:
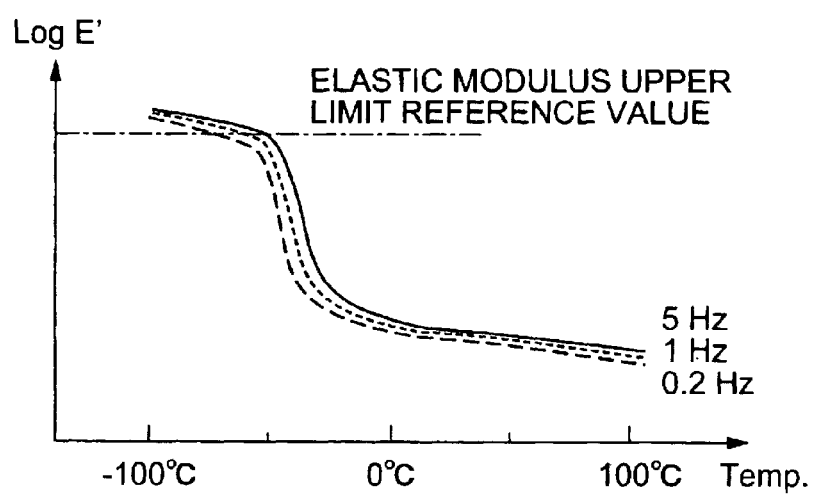
FIG. 7 is a drawing showing an example of a result of the measurement of viscoelasticity of rubber.

The detection measurement AC power program is a program made by taking out one highest frequency from the frequency lists included in the AC power program shown in FIG. 7. In general, the elastic module of almost all samples increase in proportion to the frequency of stress, so that, when the measurement of the sample can be conducted at a certain frequency, the measurement operation can necessarily be conducted at a frequency lower than the mentioned frequency. Therefore, the detection measurement operation may be conducted with respect to the largest frequency alone. This enables the time needed to conduct a detection measurement operation to be reduced greatly as compared with that needed to conduct detection measurement at a plurality of frequencies.

When the measurement executable temperature detection measurement control unit 16 receives a measurement executable temperature detection measurement starting instruction from the operator, the control unit first prepares a detection measurement temperature program on the basis of the temperature program in the temperature program retainer 17 and the detection temperature increasing speed in the detection measurement condition retainer 18, sets this program in the temperature program function generator 10, selects a detection measurement frequency from the AC power programs in the AC power program retainer 19, and sets the selected frequency in the AC power program function generator 12.

The measurement executable temperature detection measurement control unit 16 then outputs an operation starting instruction to the temperature program function generator 10 and AC power program function generator 12, and starts a detection measurement operation. When the detection measurement operation is started, the measurement executable temperature detection measurement controller 16 monitors an output from the viscoelastic modulus calculator 14. Immediately after the detection measurement operation is started, the viscoelastic modulus calculator 14 usually outputs an error mark of "non-measurement-executable" because the sample is hard. When the detection measurement temperature program progresses, so that the sample is softened, a normal elastic modulus value comes to be outputted. When the measurement executable temperature detection measurement control unit senses that the output from the viscoelastic modulus calculator 14 has a normal elastic modulus value, the temperature at this time is stored as a modulus measurable temperature, and an operation finishing instruction is then outputted to the temperature program function generator 10 and AC power program function generator 12 and thus the detection measurement is finished.

When the detection measurement finishes, the measurement executable temperature detection measurement control unit 16 prepares a new main measurement temperature program on the basis of the above-mentioned measured elastic modulus measurable temperature. As shown in FIG. 4 and FIG. 5, in the main measurement temperature program, the starting temperature is an elastic modulus measurable temperature, and the parameters other than this temperature (finishing temperature and temperature increasing speed) are the same as those of the temperature program retained in the temperature program retainer 17. Only the starting temperature out of the temperature program retained in the temperature program retainer 17 is reset to a measurement-executable temperature determined as mentioned above. The measurement executable temperature detection measurement control unit 16 sets the prepared main measurement temperature program in the temperature program function generator 10, and the AC power program in the AC power program retainer 19 in the AC power program function generator 12, and thereafter outputs a measurement starting instruction to the main measurement control unit 15, the measurement operation being thereby carried out.

Thus, a practical measurement operation is carried out on the basis of the main measurement temperature program and AC power program.

When the output from the viscoelastic modulus calculator 14 continues to be an error mark of "non-measurement-executable" until the detection measurement temperature program finishes, the measurement executable temperature detection measurement control unit 16 shows the operator a message to the effect that an elastic modulus measurable temperature was not found out to result in a failure in the detection measurement operation, and finishes this measurement operation.

The measurement executable temperature detection measurement will be described in accordance with a practical measurement operation. For example, the rubber is soft at room temperature, capable of being easily subjected to bending, tensile and shearing deformation, and measurable. However, the glass transition temperature of the rubber generally used is mostly around −30° C. to −60° C. Therefore, when the rubber is cooled to around −100° C., the temperatures of almost all kinds of rubber become lower than the glass transition temperature, and an elastic modulus increases by not smaller than two figures, so that it becomes difficult that the rubber be deformed. FIG. 7 shows an example of the results of measurement of the elasticity of the rubber. Assuming that a rubber material having such viscoelastic behavior is set to the condition on which a strain signal of the rubber is in the range of levels easily measurable in the condition after the occurrence of glass transition so that a high measurement accuracy is obtained in the vicinity of room temperature. The conditions having influence upon the easiness of measuring the sample are mainly a deformation mode, shape and size of the sample. When the sample is large, a clear response can be obtained even though the sample is very soft.

Since the glass transition temperature as the viscoelastic property of a material also constitute important measurement data, the material is usually cooled to a level not higher than the glass transition temperature, and the measurement thereof is then started. When the size of this sample is too large to cause the elastic modulus to increase by not smaller than two figures, the elastic modulus exceeds an upper limit level of elastic modulus measurement in some cases. Since the temperature at which the measurement becomes able to be conducted is unknown, the attainment of a temperature at which the error mark of "non-measurement executable" is not displayed is ascertained as the temperature is increased little by little, to turn on a main measurement. Thus, a range of temperatures at which the measurement can be conducted has to be ascertained. In order to conduct the measurement of a material for the preparation of data for the management of the quality of the material, tests are made under predetermined conditions. Therefore, there are some users of the instrument who makes trial-and-error-like operations every time. These constituted the cause of demanding the automation of the measurement of a sample for the purpose of reducing a load.

The viscoelastic modulus calculator adapted to output an error mark of "non-measurement-executable" has a storage elastic modulus E' as an index. In the measurement of dynamic viscoelasticity, a loss elastic modulus E" and a value of $\tan\delta(=E''/E')$ which is a ratio of these two can also be obtained. The $\tan\delta$ is mostly smaller than 0.1 except that at a certain temperature, such as a temperature in the vicinity of the glass transition temperature. In short, this means that the $\tan\delta$ is small with E" smaller than E' extraordinarily in many cases, so that the storage elastic modulus E' is suitably used as an index for the measurement executable temperature detection measurement.

A complex elastic modulus E* is expressed as $E^*=E'+iE''$ by using E', E" and an imaginary unit i. A ratio of the magnitude of the stress which the instrument applied to the sample to that of the strain of the sample which the instrument measures is expressed by the magnitude of E*. As is understood from the fact that $\tan\delta$ is small, the magnitude of E' accounts for the greater part of that of E*. This means that the magnitude of E' accounts for the greater part of a response of the sample. According to the present invention, the time at which the complex elastic modulus is judged larger than an upper reference value in a region in which the sample is too hard is specifically effective. Therefore, it is proper that the magnitude of E' the sensitivity of which is high when the sample is hard is used as an index. The complex elastic modulus E* can also be used as the index.

Figure 8:
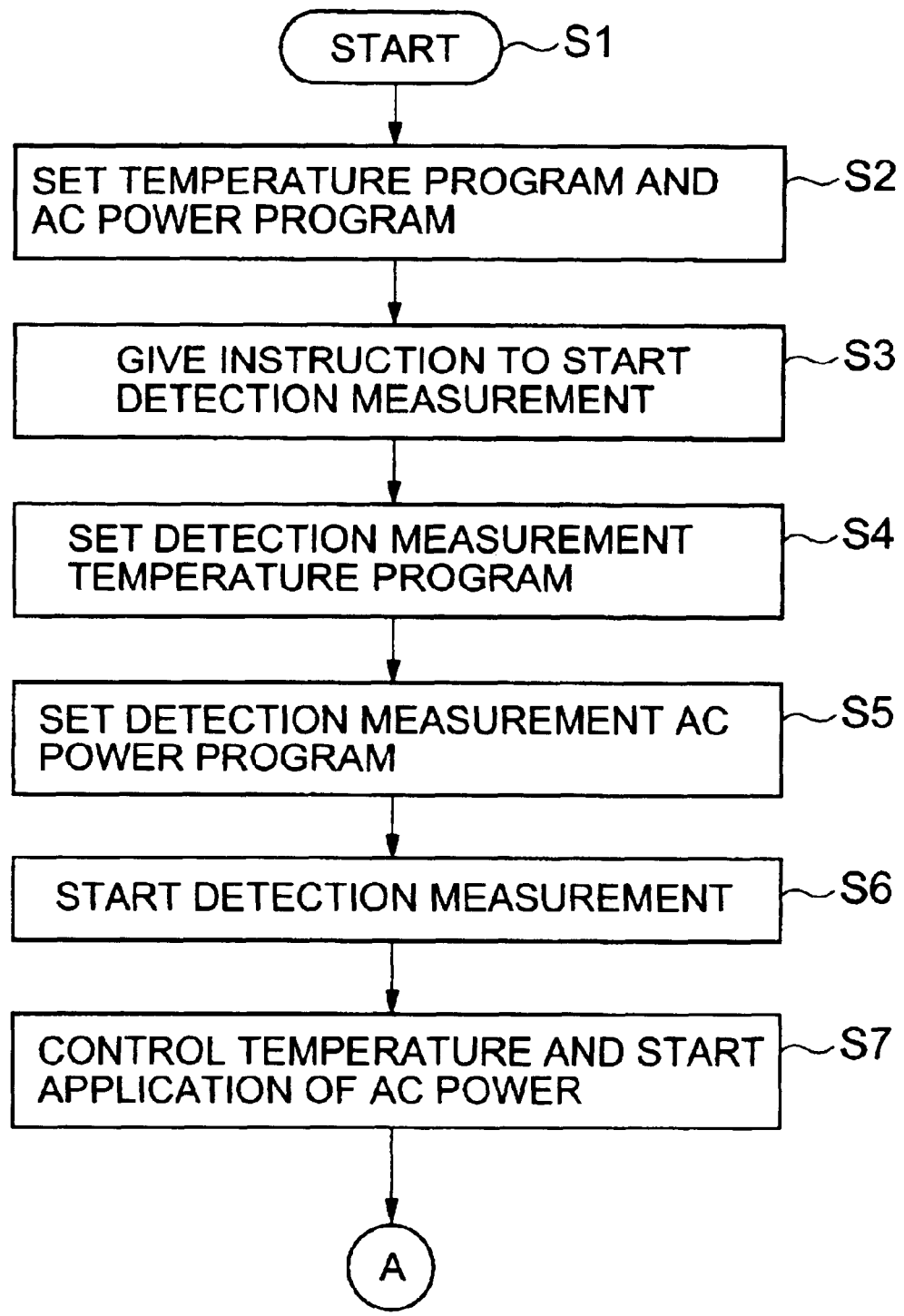
FIG. 8 is a flow chart showing an operation of the viscoelasticity measuring instrument according to the present invention.
Figure 9:
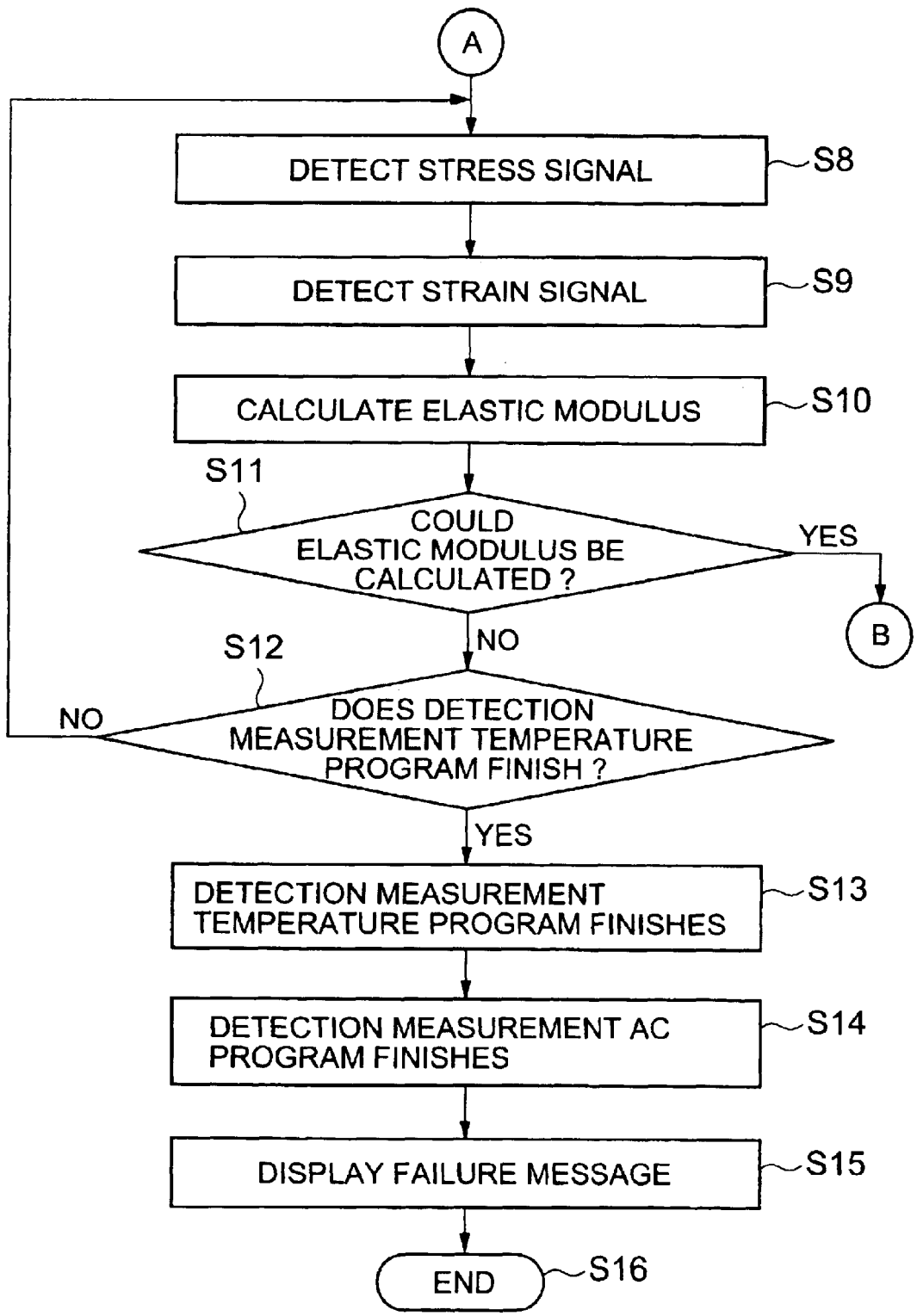
FIG. 9 is a flow chart showing an operation of the viscoelasticity measuring instrument according to the present invention.
Figure 10:
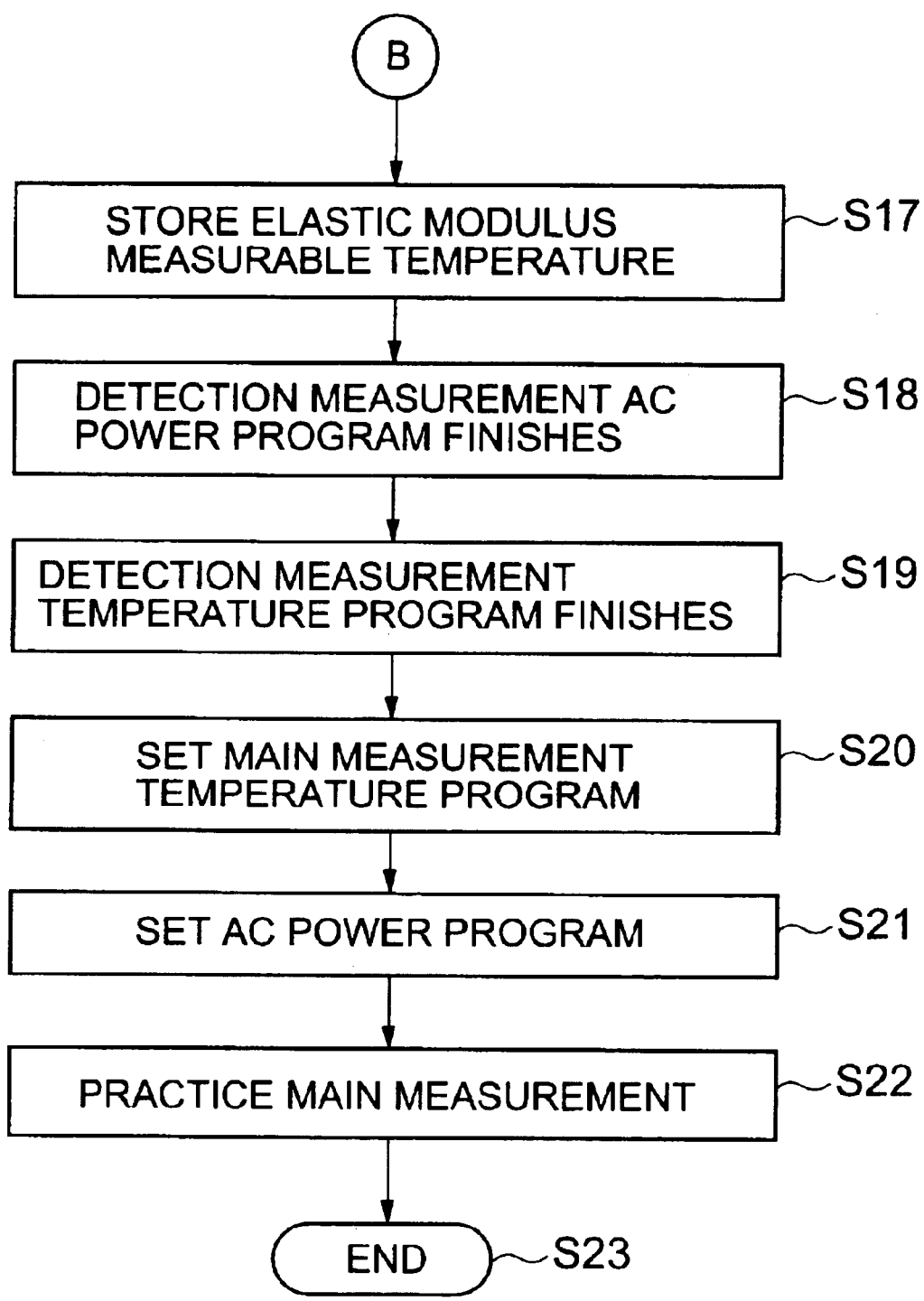
FIG. 10 is a flow chart showing an operation of the viscoelasticity measuring instrument according to the present invention.

The operation of the viscoelasticity measuring instrument according to the present invention will now be described with reference to the flow chart shown in FIG. 8.

(Step 1) The viscoelasticity measuring instrument according to the present invention starts being operated.

(Step 2) The operator sets a temperature program, an AC power program and a detection temperature increasing speed in the temperature program retainer 17, AC power program retainer 19 and detection measurement condition retainer 18 respectively.

As mentioned above, the temperature program is set so that the temperature program is started at an estimated temperature at which the sample is too hard to conduct a measurement operation.

(Step 3) The operator gives the measurement executable temperature detection measurement control unit 16 an instruction to start a detection measurement operation.

(Step 4) When the measurement executable temperature detection measurement control unit 16 receives the instruction to start a detection measurement operation, the control unit 16 prepares a detection measurement temperature program, and sets the program in the temperature program function generator 10.

(Step 5) The measurement executable temperature detection measurement control unit 16 prepares a detection measurement AC power program, and sets the program in the AC power program function generator 12.

(Step 6) The measurement executable temperature detection measurement control unit 16 outputs an instruction to start an operation to the temperature program function generator 10. The controlling of the temperature in the heating furnace is started.

(Step 7) The measurement executable temperature detection measurement control unit 16 outputs an instruction to start an operation to the AC power program function generator 12. The application of AC power to the sample is started.

From this point in time, a detection measurement operation in accordance with the detection measurement temperature program and detection measurement AC power program is started.

The measurement operation thereafter enters a detection measurement control loop including (Step 8) to (Step 12).

(Step 8) The AC power control unit 11 outputs the magnitude of the AC power applied to the sample as a stress signal to the viscoelastic modulus calculator 14.

(Step 9) The displacement detector 13 outputs the displacement of the sample detected by the differential transformer 7 and core 8 as a strain signal to the viscoelastic modulus calculator 14.

(Step 10) The viscoelastic modulus calculator 14 determines a complex modulus of the sample on the basis of the correlation between the stress signal and strain signal, and outputs the complex modulus to the measurement executable temperature detection measurement control unit 16. When the sample is so hard or so soft that the elastic modulus does not enter a calculable range, an error mark of "non-measurement-executable" is outputted.

(Step 11) The measurement executable temperature detection measurement control unit 16 judges whether a normal elastic modulus or an error mark of "non-measurement-executable" is inputted. When a normal elastic modulus is inputted, the measurement operation advances to Step 17. When an error of "non-measurement-executable" is inputted, the measurement operation advances to Step 12, and the detection measurement control loop is continued.

(Step 12) When the detection measurement temperature program does not finish, the measurement operation returns to Step 8, and the detection measurement control loop is continued. When the detection measurement temperature program finishes in Step 12, it indicates that the measurement executable temperature could not be detected in the temperature range of the detection measurement temperature program. In such a case, the measurement executable temperature detection measurement control unit 16 outputs (Steps 13, 14) an operation finishing instruction to the temperature program function generator 10 and AC power program function generator 12 to display (Step 15) a message to the effect that the measurement executable temperature could not be detected, and finish (Step 17) the detection measurement operation.

(Step 17) When a normal elastic modulus is inputted from the viscoelastic modulus calculator 14 into the measurement executable temperature detection measurement control unit 16 in Step 11, the actual temperature of the sample is stored as a lower limit (or an upper limit) value of the elastic modulus measurable temperature.

(Step 18) The measurement executable temperature detection measurement control unit 16 outputs a finishing instruction to the temperature program function generator 10 to finish the detection measurement temperature program.

(Step 19) The measurement executable temperature detection measurement control unit 16 outputs a finishing instruction to the AC power program function generator 12 to finish the detection measurement AC power program.

(Step 20) The measurement executable temperature detection measurement control unit 16 prepares a main measurement temperature program having as a starting temperature the elastic modulus measurable temperature stored in Step 17, and set the program in the temperature program function generator 10.

(Step 21) The measurement executable temperature detection measurement control unit 16 sets the frequency list and frequency mode, which are included in the AC power program in the AC power program retainer 19, in the AC power program function generator 12. Namely, a decision whether a plurality of frequencies included in the frequency list are given continuously as AC power, or a decision whether a synthetic wave thereof is given as AC power is set.

(Step 22) The measurement executable temperature detection measurement control unit 16 outputs a measurement starting instruction to the main measurement control unit 15. When the main measurement control unit 15 receives the measurement starting instruction, the control unit 15 conducts a main measurement operation practically by controlling the temperature program function generator 10 and AC power program function generator 12. Thus, the complex elastic modulus measurement (the viscoelasticity measurement) based on the main measurement temperature program is carried out.

(Step 23) The viscoelasticity measuring instrument according to the present invention finishes its operation.

In this embodiment, a stress control type viscoelasticity measuring instrument is described. A strain control type viscoelasticity measuring instrument can also be practiced in the same manner.

According to the present invention, even a sample the elastic modulus measurable temperature of which is unknown can be subjected to measurement by automatically finding out a measurement executable temperature. Therefore, it is unnecessary to find out a measurement executable temperature many times by another's hand, and the labor saving and the reduction of working hours can be attained.

Since the measurement executable temperature detection measurement control unit is provided besides the main measurement control unit, the measurement executable temperature detection becomes able to be carried out by an arbitrary temperature program or an arbitrary AC power program. This enables the measurement executable temperature to be detected at a high speed and with a high accuracy as necessary.

In the detection measurement AC power program, the highest frequency alone out of a plurality of frequencies included in the frequency list is used, so that the detection of the measurement executable temperature can be carried out at a high speed.

What is claimed is:

1. A viscoelasticity measuring instrument comprising:

a heating furnace for heating a sample;

a temperature program function generator for generating a temperature program function in accordance with a set temperature program;

a heating furnace control unit connected to the temperature program function for controlling a heating temperature of the heating furnace in accordance with the temperature program function generated by the temperature program function generator;

stress application means for applying stress to the sample;

an AC power program function generator for generating a sine wave signal as an AC power program function in accordance with a set AC power program;

an AC power control unit connected to the AC power program function generator or outputting a sine wave stress signal in accordance with the AC power program function generated by the AC power program function generator and for controlling the stress application means so that a sine wave stress corresponding to the sine wave stress signal is outputted to the stress application means for application of the sine wave stress to the sample;

a displacement detector for detecting as a sine wave strain signal a displacement of the sample occurring due to the application of a sine wave stress to the sample by the stress application means;

a viscoelastic modulus calculator for calculating a complex elastic modulus of the sample in accordance with a correlation between a sine wave stress signal outputted from the AC power control unit and a sine wave strain signal detected by the displacement detector, for outputting the complex elastic modulus as a viscoelastic modulus signal, and for outputting an error signal indicating that measurement of an elastic modulus of the sample cannot be carried out when the complex elastic modulus exceeds a preset upper limit reference level or falls below a preset lower limit reference level;

a measurement executable temperature detection measurement control unit for setting prior to a measurement operation a predetermined temperature program in the temperature program function generator, setting a predetermined AC power program in the AC power program function generator, operating the temperature program function generator and AC power program function generator and monitoring an output from the viscoelastic modulus calculator while the error signal is displayed, and outputting a measurable temperature as an upper limit temperature or a lower limit temperature at which the elastic modulus of the sample can be measured when the error signal ceases to be displayed; and a main measurement control unit for conducting a measurement operation by rewriting a temperature range in the predetermined temperature program set by the measurement executable temperature detection measurement control unit to a measurement executable temperature range in accordance with the measurable upper limit temperature or lower limit temperature outputted from the measurement executable temperature detection measurement control unit, resetting the temperature program to a desired temperature program and AC power program, outputting the temperature program and the AC power program to the temperature program function generator and AC power program function generator, respectively, and monitoring an output from the viscoelastic modulus calculator.

2. A viscoelasticity measuring instrument according to claim 1; wherein the measurement executable temperature detection measurement control unit sets a temperature increasing program in the temperature program function generator and carries out a detection measurement operation to determine a lower limit temperature at which the elastic modulus of the sample can be measured.

3. A viscoelasticity measuring instrument according to claim 1; wherein the measurement executable temperature detection measurement control unit sets a cooling program in the temperature program function generator and carries out a detection measurement operation to determine an upper limit temperature at which the elastic modulus of the sample can be measured.

4. A viscoelasticity measuring instrument according to claim 1; wherein the AC power program includes a plurality of frequencies for use during a measurement operation; and wherein the measurement executable temperature detection measurement control unit sets into the AC power program generator a frequency corresponding to a frequency from the AC power program which has the largest value.

5. A viscoelasticity measuring instrument according to claim 1; wherein a rate of temperature variation of the temperature program set in the temperature program generator by the measurement executable temperature detection measurement control unit is larger than that used in a measurement operation.

6. A viscoelasticity measuring instrument according to claim 1, wherein a rate of temperature variation of the temperature program set in the temperature program generator by the measurement executable temperature detection measurement control unit is smaller than that used in a measurement operation.

7. A viscoelasticity measuring instrument according to claim 1; wherein an output from the viscoelastic modulus calculator monitored by the measurement executable temperature detection measurement control unit comprises a stored elastic modulus.

8. A viscoelasticity measuring instrument according to claim 1; wherein the AC power generator comprises a coil and a magnet surrounding the coil.

9. A viscoelasticity measuring instrument according to claim 8; further comprising a probe having a first end portion for connection to the sample and a second end portion connected to the coil.

10. A viscoelasticity measuring instrument comprising:

heating means for heating a sample;

a temperature program function generator for generating a temperature program function in accordance with a set temperature program;

a first control unit for controlling a heating temperature of the heating means in accordance with the temperature program function;

stress application means for applying a stress to the sample;

an AC power program function generator for generating an AC power program function in accordance with a set AC power program;

a second control unit for outputting a stress signal in accordance with the AC power program function and for controlling the force application means to apply a stress corresponding to the stress signal to the sample;

displacement detecting means for detecting as a strain signal a displacement of the sample resulting from application of a stress by the stress application means;

a viscoelastic modulus calculator for calculating a complex elastic modulus of the sample in accordance with a correlation between the stress signal outputted from the second control unit and the strain signal detected by the displacement detecting means, and for outputting an error signal indicating that measurement of an elastic modulus of the sample cannot be carried out when the complex elastic modulus exceeds a preset upper limit reference level or falls below a preset lower limit reference level;

a third control unit for setting prior to a measurement operation a predetermined temperature program in the temperature program function generator, setting a predetermined AC power program in the AC power program function generator, operating the temperature program function generator and AC power program function generator and monitoring an output from the viscoelastic modulus calculator while the error signal is displayed, and outputting a measurable temperature as an upper limit temperature or a lower limit temperature at which the elastic modulus of the sample can be measured when the error signal ceases to be displayed; and a fourth control unit for conducting a viscoelasticity measurement operation by rewriting a temperature range in the predetermined temperature program set by the third control unit to a measurement executable temperature range in accordance with the measurable upper limit temperature or lower limit temperature outputted from the third control unit, resetting the temperature program to a desired temperature program and AC power program, outputting the desired temperature program and the AC power program to the temperature program function generator and AC power program function generator, respectively, and monitoring an output from the viscoelastic modulus calculator.

11. A viscoelasticity measuring instrument according to claim 10; wherein the AC power generator comprises a coil and a magnet surrounding the coil.

12. A viscoelasticity measuring instrument according to claim 11; further comprising a probe having a first end portion for connection to the sample and a second end portion connected to the coil.

13. A viscoelasticity measuring instrument according to claim 10; wherein the displacement detecting means detects a displacement of the sample selected from the group consisting of bending displacement, tension displacement, compression displacement, shearing displacement, and torsion displacement.

14. A viscoelasticity measuring instrument according to claim 10; further comprising a probe having a first end portion for connection to the sample and a second end portion.

15. A viscoelasticity measuring instrument according to claim 14; further comprising a core mounted on the probe between the first and second end portions thereof, and a differential transformer surrounding the core.

16. A viscoelasticity measuring instrument according to claim 15; wherein the displacement detecting means includes means for detecting as the strain signal a displacement between the core and the differential transformer.

* * * * *